United States Patent [19]

Conlon et al.

[11] Patent Number: 4,960,126
[45] Date of Patent: Oct. 2, 1990

[54] ECG SYNCHRONIZED PULSE OXIMETER

[75] Inventors: Brendan Conlon, Elm Grove; James A. Devine; James A. Dittmar, both of Waukesha, all of Wis.

[73] Assignee: Criticare Systems, Inc., Waukesha, Wis.

[21] Appl. No.: 259,446

[22] Filed: Oct. 14, 1988

Related U.S. Application Data

[63] Continuation of Ser. No. 144,913, Jan. 15, 1988, abandoned.

[51] Int. Cl.$^5$ .............................................. A61B 5/02
[52] U.S. Cl. .................................. 128/633; 128/666; 128/700
[58] Field of Search ............................. 128/633–634, 128/637, 664–667, 700, 708; 356/39–41

[56] References Cited

U.S. PATENT DOCUMENTS

| | | | |
|---|---|---|---|
| 3,858,574 | 1/1975 | Page | 128/666 |
| 4,181,134 | 1/1980 | Mason et al. | 128/689 |
| 4,425,921 | 1/1984 | Fujisaki et al. | 128/664 X |
| 4,425,922 | 1/1984 | Conti et al. | 128/700 X |
| 4,545,387 | 10/1985 | Balique | 128/664 X |
| 4,641,658 | 2/1987 | Lepper | 128/633 |
| 4,651,741 | 3/1987 | Passafaro | 128/637 X |
| 4,653,498 | 3/1987 | New, Jr. et al. | 128/666 X |
| 4,685,464 | 8/1987 | Goldberger et al. | 128/666 X |
| 4,694,833 | 9/1987 | Hamaguri | 128/666 X |
| 4,788,982 | 12/1988 | Gedeon et al. | 128/666 X |
| 4,802,486 | 2/1989 | Goodman et al. | 128/687 X |

FOREIGN PATENT DOCUMENTS

WO86/05674 10/1986 PCT Int'l Appl.

OTHER PUBLICATIONS

"Digital Enhancement of the Peripheral Admittance Plethysmogram", by Lloyd A. Marks, Member, IEEE, IEEE Transactions On Biomedical Engineering vol. BME-34, No. 3, Mar. 1987, pp. 192-198.
Nellcor Redefines Pulse Oximetry, Introducing the Nellcor N-200 With ECG Synchronization, Hayward, California.

*Primary Examiner*—Angela D. Sykes
*Attorney, Agent, or Firm*—Willian Brinks Olds Hofer Gilson & Lione

[57] ABSTRACT

A pulse oximeter and method of determining the oxygen saturation level of a patient's blood wherein a heartbeat related signal is used, as a reference to guide the averaging of optical pulse waveforms. The oximeter and method assign different weighting to different optical pulses based upon the amplitude of new pulse waveforms and the degree of similarity between it and the preceding waveform. A composite, averaged pulse waveform is then used in computing oxygen saturation level.

15 Claims, 9 Drawing Sheets

FIG_14

FIG-15

ECG SYNCHRONIZED PULSE OXIMETER

This application is a continuation of application Ser. No. 07/144,913, filed Jan. 15, 1988, now abandoned.

FIELD OF THE INVENTION

This invention relates in general to pulse oximetry. It relates specifically to the reduction of noise and artifact in a pulse oximeter by the use of a correlated ECG signal.

DESCRIPTION OF THE PRIOR ART

Oxygen saturation level is an important measure of a patient's well-being. It is of value during many surgical and anesthetic procedures. Pulse oximetry is a well-known means of measuring the oxygen saturation level of blood, non-invasively, by measuring the pulsatile modulation of two beams of light of different wavelengths as they pass through body tissue, a finger, for example.

The beams of light are applied and detected by a sensor containing light emitting diodes and a photodetector. An oximeter computes saturation depending upon the relative magnitudes of the AC components of the two absorption waveforms or plethysmographs. These AC components are, in general, small compared to the magnitude of the total waveform (AC+DC components) representative of total absorption present. Any motion of the finger relative to the sensor results in perturbations of the plethysmographs known as motion artifact, which may cause the computed saturation value to be in error. In addition, in poorly perfused patients the circulation may not adequately modulate the light beams to the point where they can be distinguished from system noise.

Most commercial pulse oximeters determine the amplitude of the plethysmographs utilizing only the information contained in each waveform, itself. Algorithms currently in use must determine both the period and amplitude of each plethysmograph by analyzing such waveform parameters as slope transition, minima and maxima, and rise and fall time. Additionally, such algorithms may employ decision rules in order to reject data which falls outside of certain limits.

A major problem with these algorithms is that in searching for peak waveform excursions they inherently maximize the influence of motion artifact. While in many circumstances these algorithms perform adequately, the presence of motion artifact may disrupt their function to the point where either the majority of the data is rejected or an erroneous saturation value is calculated.

To compensate for this inadequacy, the computed saturation value is conventionally often averaged with several recent values in order to reduce the disruptive effect of corrupted data. Such averaging is only useful if the number of bad data values is small relative to the number of good data values. Thus, the usefulness of most commercial pulse oximeters is limited to situations in which the patient is well perfused and subject to minimal (or isolated instances of) motion.

Recently, Nellcor Incorporated introduced a pulse oximeter which seeks to overcome this problem. This oximeter's operation involves the synchronization of the plethysmographs with an ECG signal. The ECG signal is used to determine the period of the plethysmographs and to guide the measurement of the peak and valley values from which the AC components and, ultimately, oxygen saturation are computed. By fixing the temporal location of the peak and valley sampling relative to the R-wave of the ECG, this solution eliminates the error introduced by searching for peaks in the presence of artifact. However, it fails to reduce the level of such artifact present in the plethysmographs at the peak and valley locations.

SUMMARY OF THE INVENTION

It is an object of the present invention to provide a new and improved pulse oximetry method which greatly minimizes the effects of motion artifact and poor perfusion in computed saturation readings.

Another object is to provide an oximeter and method which use a correlated signal to reduce the effect of motion artifact by increasing the signal-to-noise ratio of the plethysmographs through the use of ensemble averaging.

Yet another object is to provide an oximeter and method which utilize a correlated ECG signal for this purpose.

A further object is to provide an oximeter and method which increase the validity of readings obtained from poorly-perfused patients by increasing the signal-to-noise ratio of the plethysmographs through the use of ensemble averaging.

Still another object is to provide an oximeter and method which distinguish those pulses which are contaminated with motion artifact from those which are not, and distinguishes those pulses which are the result of low perfusion from those which are not, and applies a varying degree of averaging limited to the extent necessary to improve signal quality to a usable level.

The foregoing and other objects of the invention are realized by providing a pulse oximeter including a sensor for the emission and detection of two beams of light of different wavelengths. The beams are passed through skin tissue and modulated by the flow of blood therein. The preferred embodiment includes an apparatus for the amplification and detection of an ECG, R-wave signal. This signal is used as a reference to guide the averaging of subsequent optical pulse waveforms. The weight given to the newest pulse waveform during the averaging process is determined by the amplitude of that pulse waveform and by the degree of similarity between it and the preceding pulse waveform. The composite, averaged pulse waveform is then used in computing the oxygen saturation of the blood.

BRIEF DESCRIPTION OF THE DRAWINGS

The invention, including its construction and method of operation, is illustrated more or less diagrammatically in the following drawings, in which.

FIG. is a diagram of three sets of pulsatile waveforms illustrating calculation steps employed by the software of the present invention.

DETAILED DESCRIPTION OF THE PREFERRED EMBODIMENT

Figure 1:
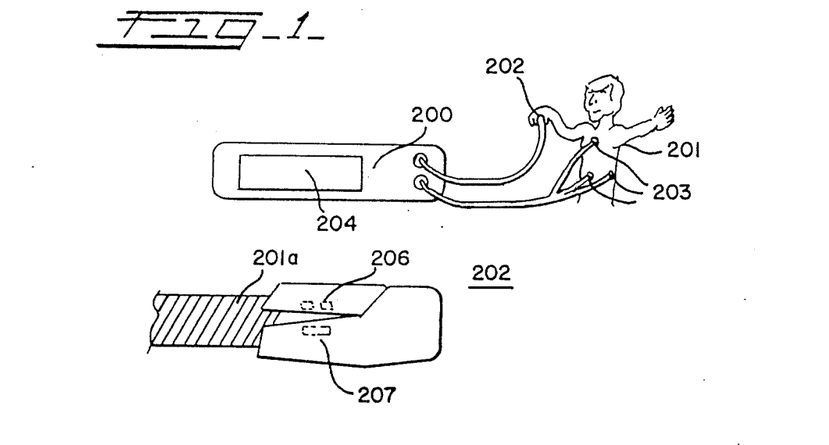
FIG. 1 is a diagrammatic illustration of an oximeter embodying features of the present invention attached to a patient, with attachment to the patient's finger shown in an enlarged inset.

Referring now to the drawings, and particularly to FIG. 1, a pulse oximeter 200 is shown connected to a patient 201. The oximeter 200 includes an optical sensor 202 containing red and infra-red LEDs 206, and a photodetector 207. The sensor 202 is placed in contact with the finger 201a of a patient and provides the pulse oximeter 200 with red and infra-red plethysmographic waveforms.

The patient 201 also wears three standard ECG electrodes 203 which provide the pulse oximeter 200 with an ECG signal. The ECG signal, if present, is used to enhance the quality of the optical waveforms. The oximeter 200 computes oxygen saturation from the enhanced waveforms and displays it digitally on a screen 204. As will hereinafter be discussed, the oximeter 200 is also capable of displaying other information on the screen 204.

Figure 2:
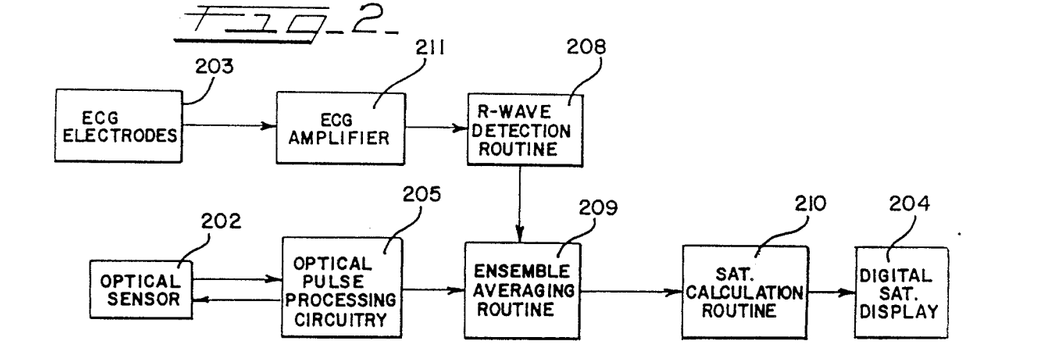
FIG. 2 is a block diagram illustration of oximeter components and their relationship.
Figure 3:
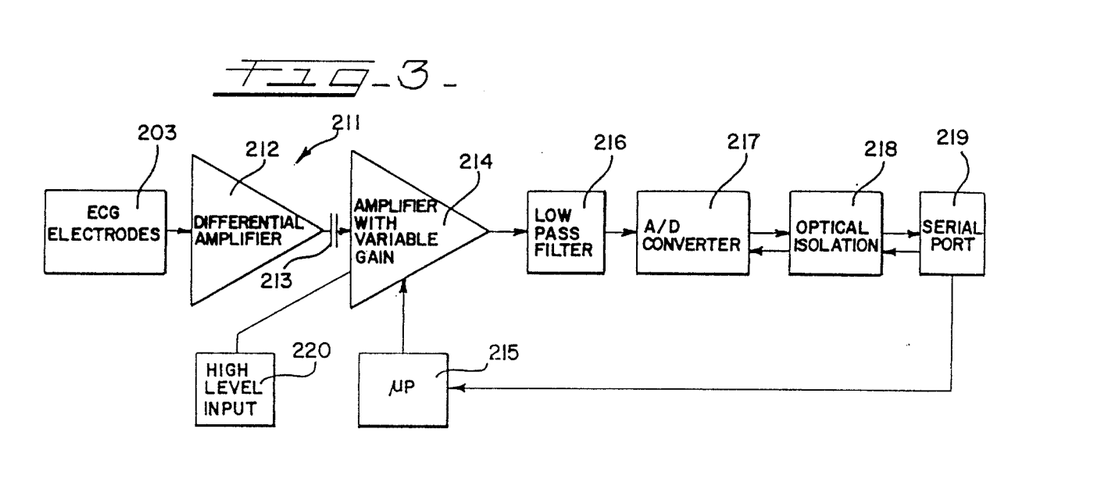
FIG. 3 is a block diagram illustration of the ECG processing component, its sub-components, and their relationship.

Referring now to FIGS. 2 and 3, as well as FIG. 1, the major components of the pulse oximeter 200 are illustrated in block diagram. Generally speaking, according to the invention, an optical pulse processing circuit 205 of a type hereinafter discussed drives the red and infra-red LEDs 206, and derives red and infra-red plethysmographic waveforms from the output of photodetector 207. An ECG amplifier 211 and an R-wave detection algorithm routine 208 process the ECG signal provided by electrodes 203, and determine the timing for an ensemble averaging algorithm routine 209. An oxygen saturation value is calculated by a microcomputer 215 in a calculation algorithm routine 210 using the ensemble averaged waveform as input, and is then displayed digitally on a screen 204.

If an ECG signal is not present, the lack thereof is recognized in the R-wave detection algorithm routine 208, which causes an ensemble averaging algorithm routine 209 to be bypassed and the unenhanced optical pulse to be input into the calculation algorithm routine 210. The microcomputer 215 executes software comprising the R-wave detection, ensemble averaging, calculation, and display algorithm routines.

FIG. 3 is a block diagram illustrating the ECG amplifier 211 in greater detail. The three-lead ECG signal is amplified by differential amplifier 212. This amplifier 212 amplifies the differential component of the signal, which is the desired ECG waveform, while rejecting a large portion of the common-mode voltage.

The output of this amplifier 212 is AC-coupled, by capacitor 213, to amplifier 214, which provides further gain. The gain provided by amplifier 214 is adjustable and can be set to ½, 1 or 2 by microcomputer 215. Amplifier 214 can also accept an additional high level input 220, which is intended to be connected to the output of an external ECG monitoring device, thus obviating the need for an additional set of ECG electrodes on the patient.

The output of amplifier 214 is processed by low-pass filter 216 to remove unwanted artifact such as 60HZ and electrocautery induced noise, and is converted to a serial, digital signal by A/D converter 217. The digitized signal then passes through opto-isolator 218 to serial port 219 which resides on the bus of the microcomputer 215. The opto-isolator 218 serves to isolate the patient ECG leads from the external power supply, and is incorporated for reasons of patient safety.

Figures 4, 7, 9:
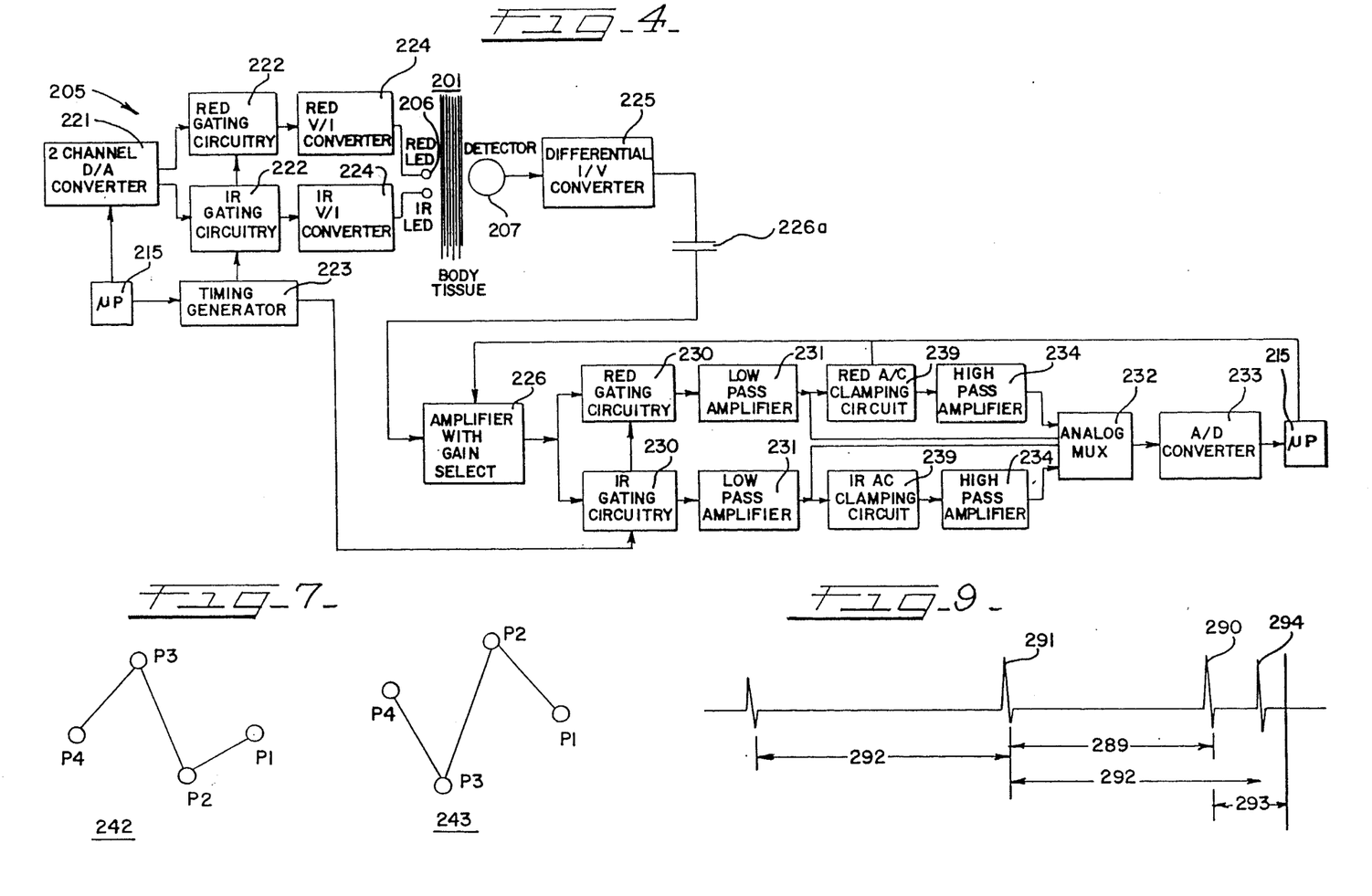
FIG. 4 is a block diagram illustration of the optical pulse processing component, its subcomponents, components, and their relationship.
FIG. 7 is an illustration of two ECG waveform templates utilized by the R-wave detection algorithm.
FIG. 9 is a block diagram of an R-wave artifact rejection timing sub-routine utilized in the software of the present invention.

Referring now to FIG. 4, a block diagram describing the optical pulse processing circuit 205 is illustrated in greater detail. The microcomputer 215 transmits desired red and infra-red LED drive values to a two-channel D/A converter 221. The two output channels of the D/A converter 221 are alternately selected by gating circuit 222, producing pulse trains 227 and 228 (illustrated in FIG. 5).

The pulse trains 227 and 228 drive voltage-to-current converters 224 which provide current sources to drive the red and infra-red LEDs 206. The action of the gating circuitry is controlled by a timing generator 223. The beams of light produced by the LEDs 206 pass through skin tissue 207 in the patient's finger 201a and are modulated by the flow of blood therein.

The modulated light excites photodetector 207 which produces an output current varying in accordance with the incident light. The current is converted to voltage and amplified by an I/V converter 225. A differential realization of the I/V converter is utilized to maximize the supply margins for a given gain, thereby decreasing the likelihood of saturating the amplifier with ambient light, before the signal can be AC-coupled by capacitor 226a.

The AC-coupled output of the I/V converter 225 is amplified by an amplifier 226 which incorporates gain selection circuitry controlled by microprocessor 215. The output of amplifier 226 is the composite signal 229, shown in FIG. 5, and is a superposition of the modulated red and infra-red pulse trains 227 and 228.

The separate red and infra-red pulsatile waveforms are synchronously demodulated from the combined signal by the action of a gating circuit 230 and low-pass amplifiers 231. Synchronous demodulation requires that the gating action of circuit 230 be synchronized with that of the gating circuit 222; synchronization which is provided by the timing generator 223.

Figure 5:
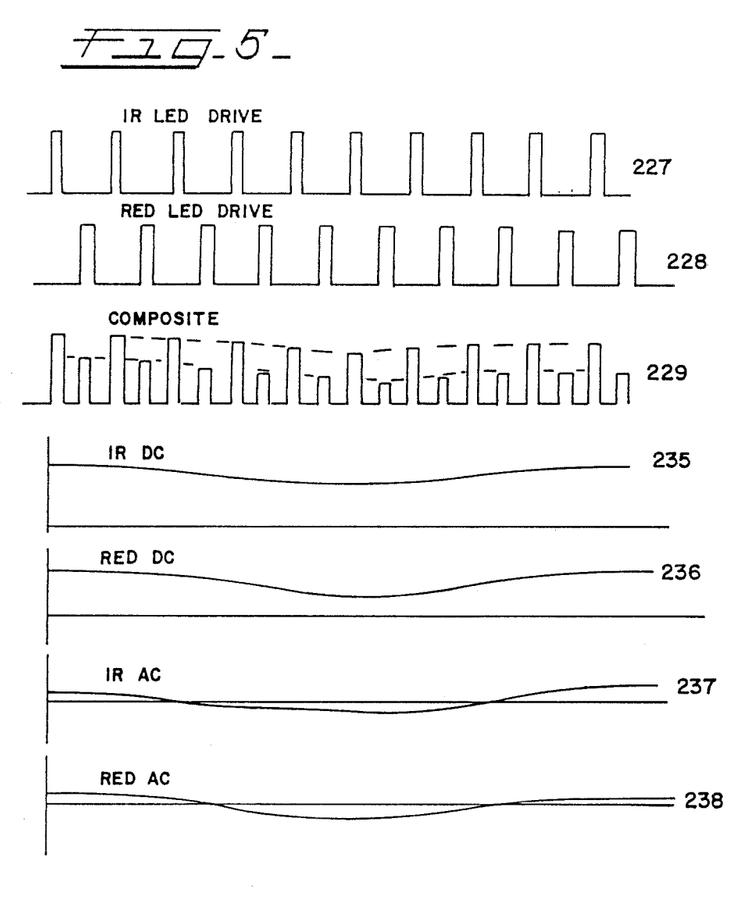
FIG. 5 is a diagrammatic illustration of red, infra-red, and composite pulsatile waveforms as utilized by the oximeter of the present invention.

The demodulated red and infra-red signals comprise the DC signals 235 and 236 shown in FIG. 5. The AC signals 237 and 238 shown there are derived by filtering and amplifying the DC signals using high-pass amplifiers 234.

Clamping circuit 239 allows the microcomputer 215 to force the input to high-pass amplifiers 234 to zero, to allow quick recovery in the event the amplifiers become saturated. Analog multiplexer 232 selects one of the four (IRAC, IRDC, RAC, RDC) signals as input to the A/D converter 233, under the control of the microcomputer 215.

The hardware of the pulse oximeter 200, including its organization and operation, has now been described in a manner which will be readily understood by those skilled in the art. The oximeter 200 is software driven and the operation of the software as it relates to the present invention will now be discussed. This includes the process of removing motion artifact and enhancing the waveform quality in low perfusion situations according to the invention.

Figure 6:
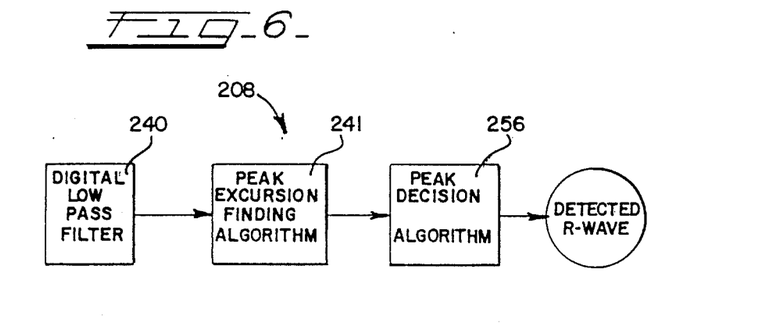
FIG. 6 is a block diagram of the R-wave detection algorithm routine in the software of the present invention.

ECG synchronization is used to provide a reliable time frame upon which to base ensemble averaging, and a robust and accurate R-wave detection algorithm routine 208 is an integral part of the invention. FIG. 6 is a block diagram illustrating the components of the R-wave detection algorithm routine 208 which is incorporated in the preferred embodiment. The R-wave detection process involves three stages of processing: a low-pass digital filter 240, a peak excursion finding algorithm routine 241, and a peak discrimination algorithm routine 256. These algorithm routines will now be discussed in detail.

Referring again to FIG. 3, the ECG input signal from the A/D converter 217 is sampled via a serial port 219 at a rate of 240HZ. The resulting digital waveform is low-pass filtered, with a cut-off frequency of 12HZ, to remove artifact such as 60HZ and muscle noise.

Figure 8:
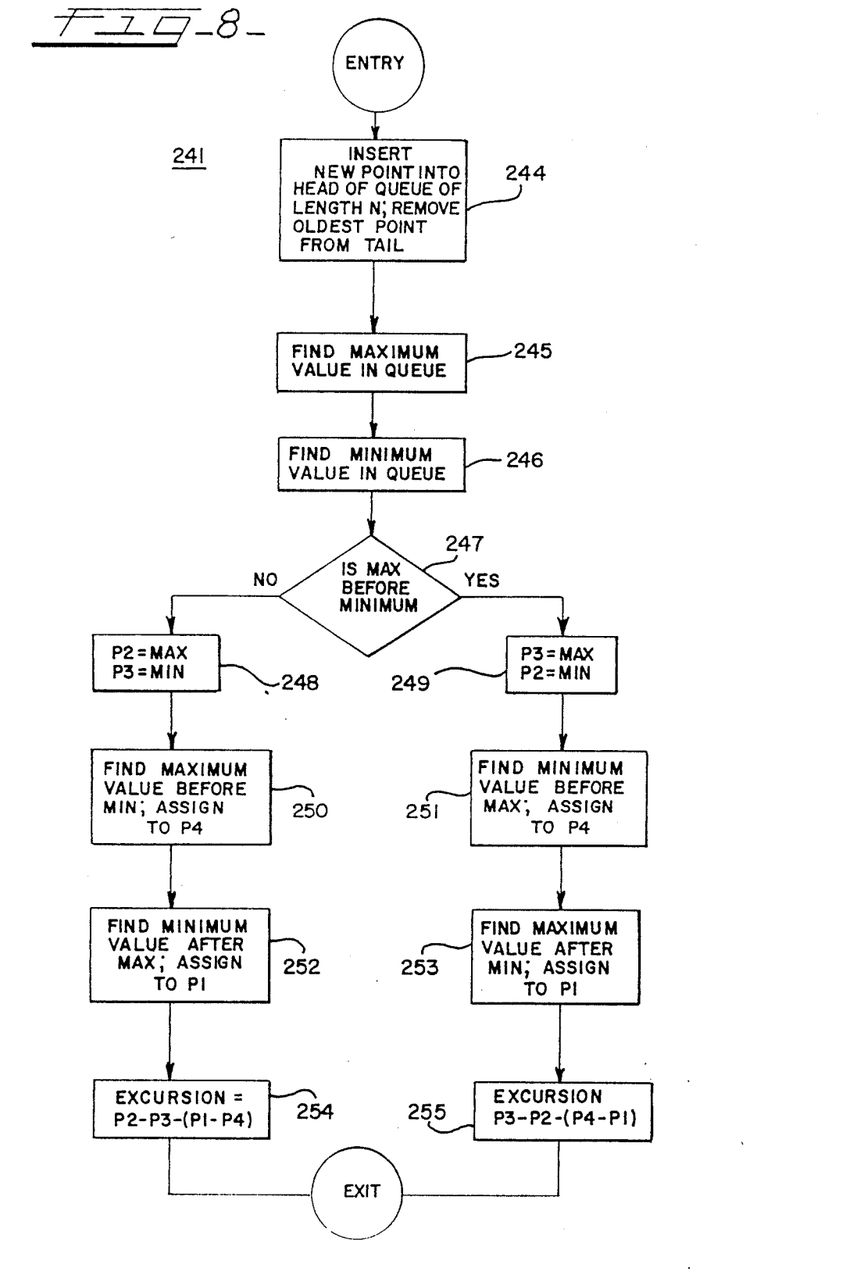
FIG. 8 is a block diagram of the R-wave peak excursion finding algorithm.

The filtered ECG waveform then undergoes transformation by the peak excursion finding algorithm routine 241 depicted in a flowchart in FIG. 8. The purpose of this transformation is to amplify those characteristics of the ECG waveform which are inherent in QRS complexes while inhibiting those which are not, QRS being the medical acronym for electrical shock instigation of the heart's contraction cycle. The algorithm routine 241 continually matches the ECG waveform to one of two templates 242 and 243 shown in FIG. 7.

In template 242, P3 is the maximum value within the interval N, and P2 is the minimum. P4 is the minimum value to the left of P3, and P1 is the maximum value to the right of P2. Note that the relations $P3 >= P2$, $P1 >= P2$, and $P4 <= P3$ apply to this template.

In template 243, P3 is the minimum value within the interval N, and P2 is the maximum. P4 is the maximum value to the left of P3, and P1 is the minimum value to the right of P2. Note that the relations $P3 <= P2$, $P1 >= P2$, and $P4 >= P3$ apply to this template.

Note further that any continuous function on an interval N must map into one of these two templates. The largest closed excursion on the interval N is defined as the quantity $P3-P2-(P4-P1)$ for template 242, and $P2-P3-(P1-P4)$ for template 243. Since a QRS complex is characterized by a large positive or negative excursion followed immediately by a return to the baseline, the largest closed excursion in an interval on the order of a typical QRS duration is a good indication of the presence of an R-wave spike.

The algorithm routine 241 calls for N=8, 12, 16, 20, and 24, with individual excursion values being summed so as to give a total transformation value. More weight is placed on lower values of N in order to emphasize narrower spikes over wider ones.

The algorithm routine 241 maintains a queue, of a length N, which is searched in order to determine the parameters P1, P2, P3, and P4. Starting at the top of the flowchart diagram, block 244 describes the manipulation of the queue. The newest sample value is inserted at the head of the queue and the oldest is removed from the tail.

Next, at block 245, the queue is searched and the maximum value and its position in the queue are found. Similarly, at block 246, the queue is searched again and the minimum value and its position in the queue are found. Decision diamond 247 then determines which of the two templates 242 or 243 are matched by the current interval contained in the queue by asking the question, "Does the maximum occur before the minimum?" If it does, the waveform matches template 242; otherwise it matches template 243.

Following this, the parameters P2 and P3 are assigned the appropriate maximum or minimum values in blocks 248 and 249. Next, the value of P4 is found in block 250 or block 251. If template 242 was matched, it is given by the maximum value after P2, as in block 253. Otherwise, it is given by the minimum value before P3 as in block 252. Finally, the peak closed excursion on the interval N is computed in blocks 254 and 255 using the formula appropriate to the currently matched template.

After transformation of the ECG waveform in the manner described, the peak discrimination algorithm 256 routine (see FIG. 6) classifies the spikes found in the transformed waveform as either QRS complexes or artifact. The peak discrimination algorithm routine 256 is a state machine with three states: peak, valley, and noise peak. If the algorithm routine 256 is in the valley or noise peak state, it enters the peak state when the waveform exceeds a threshold which is based upon the past history of the ECG waveform. If the algorithm routine 256 is in the peak state, it exits this state and enters the valley state when the waveform drops below one fourth of the maximum value attained in the peak state.

If the algorithm routine 256 is in the valley state, it enters the noise peak state whenever the waveform climbs above four times the minimum value attained during the valley state. If the algorithm routine 256 is in the noise peak state, it enters the valley state whenever the waveform drops half the distance between the maximum value attained during the noise peak state and the minimum value attained during the previous valley state. The detection of a QRS spike is signalled upon the transition into the peak state.

The algorithm routine 256 maintains an average of the last eight QRS peaks in order to set the threshold for detecting the next peak in the waveform. In addition, the algorithm routine 256 maintains an average of the noise peak levels found between the last four QRS peaks, in order to aid in the rejection of artifact while accepting valid QRS spikes. These averages are updated upon the transition between the peak and valley states.

Additional rejection of artifact is gained by examining the length of time 289 which has elapsed between a new peak 290 and the last accepted peak 291, as illustrated in FIG. 9. If it is less than $\frac{3}{8}$ of the previous R—R interval 292, the spike 290 is assumed to be noise and is not counted as a QRS spike. If it is greater than $\frac{3}{8}$, but less than $\frac{7}{8}$, of the previous R—R interval 292, the spike 290 is accepted "on probation" as long as it exceeds a second threshold which takes into account the level of noise encountered during the last four beats. It is counted as a valid QRS spike but the previous state information is saved in order to "undo" acceptance of spike 290 if a better candidate is found.

A probation interval 293 is calculated in this case during which any spike 294 meeting the threshold requirement overrides the acceptance of the spike 290 in question. This probation interval is equal to 9/8 of the previous R—R interval 393, minus the length of time 289 which has elapsed since the last accepted peak 291. If the new spike 290 arrives after ⅞ of the previous R—R interval 292, it is accepted unconditionally, and no chance is allowed for a subsequent spike to override it.

Figure 10:
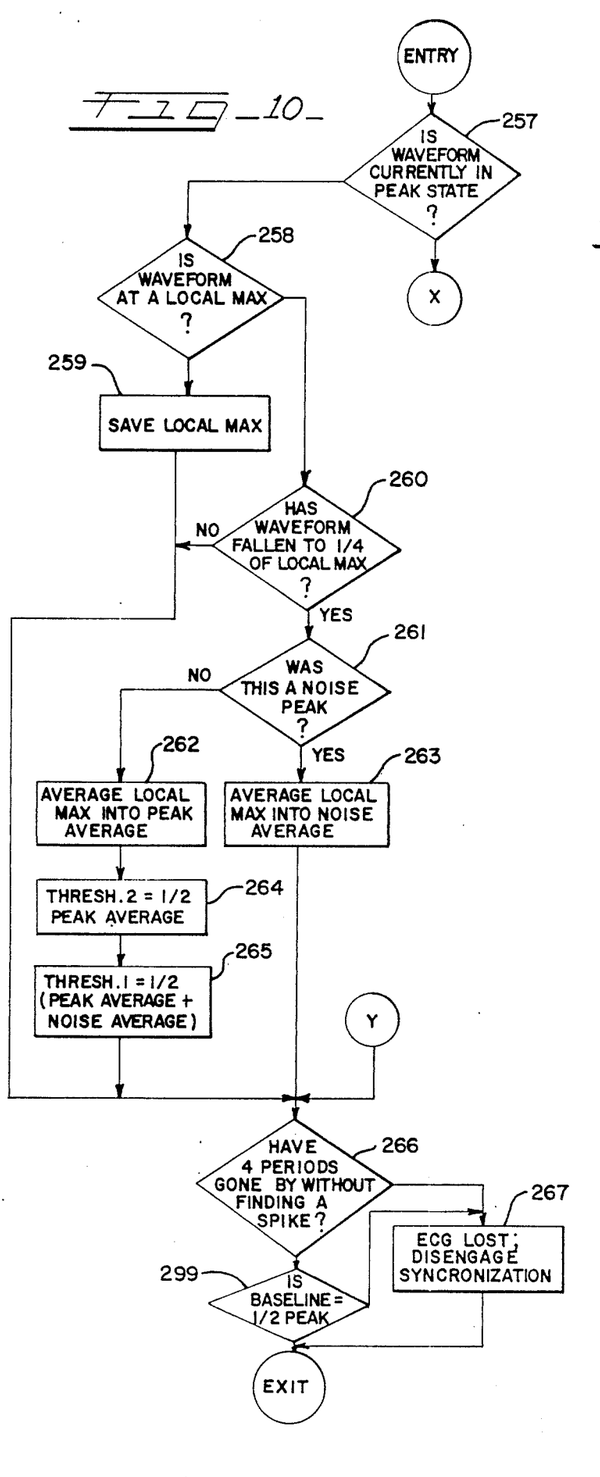
FIG. 10 is a block diagram of a portion of the R-wave peak discrimination algorithm.
Figure 11:
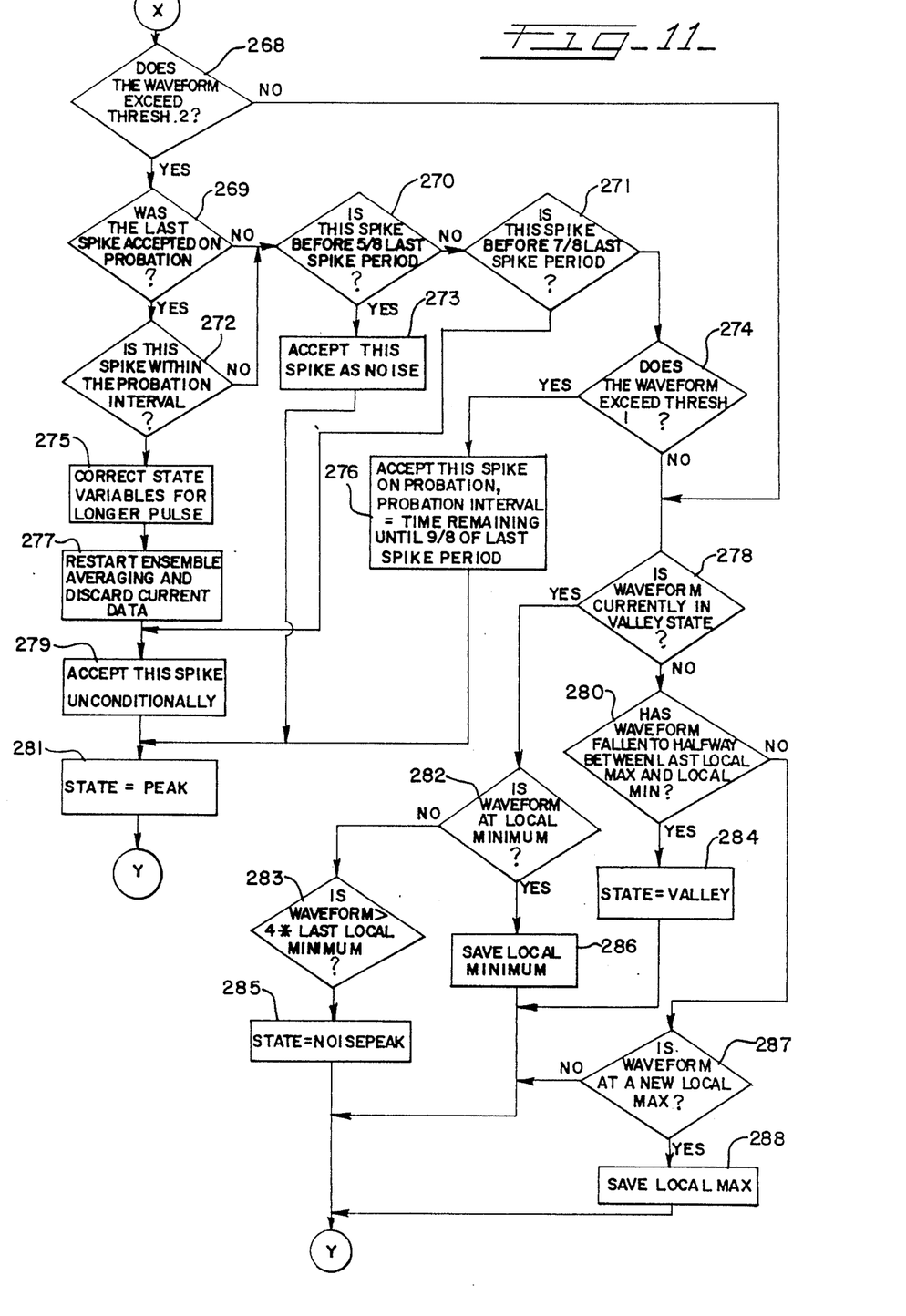
FIG. 11 is a block diagram of another portion of the R-wave peak discrimination algorithm.

FIGS. 10 and 11 illustrate flowcharts detailing the algorithm routine 256. At the top of FIG. 10 we have a decision diamond 257, which determines whether the algorithm routine 256 is in the peak state. If it is not, the algorithm routine 256 must check whether conditions are satisfied for entering this state.

This is determined in part by decision diamond 268 in FIG. 11, which asks the question, "Does the waveform exceed threshold 2?" If the waveform does not exceed this threshold, it does not enter the peak state. If it does, the algorithm routine 256 then determines the length of time 289 which has elapsed since the last accepted spike and its relationship to the previous R—R interval 292 (see FIG. 9). Decision diamond 269 first checks to see if the last spike was accepted "on probation". If it was, decision diamond 272 determines whether the current spike falls within the probation interval. If it does, block 275 corrects state variables such as the average R—R interval for the longer pulse length. Block 277 then starts the ensemble averaging with the current overriding spike 294, causing any plethysmographic data collected since the last spike 290 to be discarded. This does not substantially affect the quality of the ensemble averaged waveform since the discarded portion generally falls during the decay portion of the waveform 296 which is well after the valley 297 and peak 298 used to determine the saturation reading.

The overriding spike 294 (see FIG. 9) is then accepted unconditionally in block 279, i.e., without any chance to be itself overridden. If the last spike was not accepted on probation or the current probation interval has expired, the length of time 289 which has elapsed since the last accepted pulse must exceed ⅝ of the previous R—R interval 292. Decision diamond 270 determines whether or not this is the case. If the current pulse 290 is too soon, it is classified as noise by box 273. If the current pulse 290 is acceptable, it must then be determined whether or not it should be accepted "on probation". This is determined by decision diamond 271, which checks whether the length of time 289 elapsed since the last accepted spike exceeds ⅝ of the previous R—R interval 292.

If this is the case, block 279 accepts the pulse unconditionally. If not, decision diamond 274 checks to determine whether the waveform exceeds threshold 1, which takes into account the noise level encountered during the last four beats. If the waveform does not exceed this threshold, it does not enter the peak state. If this threshold is exceeded, the spike is accepted "on probation". Block 276 calculates the probation interval and accepts the spike. In all cases in which the spike was accepted, the peak state is entered by block 281.

If the peak state was not entered as a result of tests at decision diamonds 268 or 274, decision diamond 278 determines whether the algorithm routine 256 is in the valley or the noise peak state. If it is in the valley state, decision diamond 282 and block 286 keep track of the minimum value encountered during the valley state. If the waveform is not at a new local minimum, decision diamond 283 determines whether the noise peak state can be entered. If the waveform has climbed above four times the last local minimum set by block 286, the noise peak state is entered by block 285.

If the algorithm routine 256 is found to be in the noise peak state as a result of test 278, decision diamond 280 checks to see whether the waveform has fallen to halfway between the last local maximum saved by block 288 and the last local minimum saved by block 286. If it has, the valley state is entered by block 284. Otherwise, decision diamond 287 and block 288 keep track of the maximum value encountered during the noise peak state.

Referring again to FIG. 10, if the algorithm routine 256 was initially found to be in the peak state as a result of test 257, decision diamond 258 and block 259 keep track of the maximum value encountered during the peak state. If the waveform is not at a local maximum, decision diamond 260 then checks to see whether the waveform has fallen to one quarter of the last local maximum set by block 259. If it has, decision diamond 261 then determines whether the current peak was a noise peak or a QRS peak. If it was a noise peak, block 263 updates the average of the noise levels over the last four beats. If it was a QRS peak, block 262 then updates the average of the last eight QRS peaks using the local maximum found by block 259. It also updates the average of the noise levels over the last four beats using the largest local maximum found by block 288 since the last accepted beat.

Blocks 264 and 265 compute the threshold values needed to detect the next QRS peak. Threshold 1 is halfway between the current eight beat peak average and the current four beat noise average. Threshold 2 is one-half of the current eight beat peak average.

In all cases before exiting algorithm routine 256, parameters reflecting the quality of the ECG waveform are tested. Decision diamond 266 checks to see if the time elapsed since the spike was accepted exceeds four times the last R—R interval. Next, decision diamond 299 checks to determine whether the baseline of the transformed signal has exceeded one-half the peak value. If any of these test levels are exceeded, the ECG waveform is assumed to be lost and block 267 disengages the synchronization.

The operation of the R-wave detection algorithm routine 208 of the oximeter software has now been discussed in detail. Referring now to FIGS. 12-15, the ensemble averaging algorithm routine 209 utilizes the output of R-wave peak discrimination algorithm routine 256 to enhance that component of the red and infra-red plethysmographic waveforms which is correlated with the ECG, while diminishing all which is unrelated, to yield a signal with an improved signal-to-noise ratio.

The algorithm routine 209 relies on the assumption that instances of moderate to severe motion, and of low perfusion, can be detected as the plethysmographic waveforms are being sampled. To do this it has been found to be advantageous to buffer these waveforms while they are being sampled, and to delay the actual averaging until the next R-wave peak is detected. The averaging weight of the current waveform cycle can then be adjusted, depending upon whether the plethysmographic waveform just acquired is weak or exhibits the influence of excessive motion artifact. An additional benefit of this buffering stage is that the oximeter 200 is able to discard waveform pulses during which optical pulse processing circuitry 205 has saturated and distorted the waveform. Yet another benefit of this buffering stage is that it allows a level of error tolerance in the R-wave detection process whereby algorithm routine 256 can accept certain marginal QRS spikes "on probation", as described above, while maintaining the flexibility to correct the error if a better candidate is subsequently detected.

Figure 13:
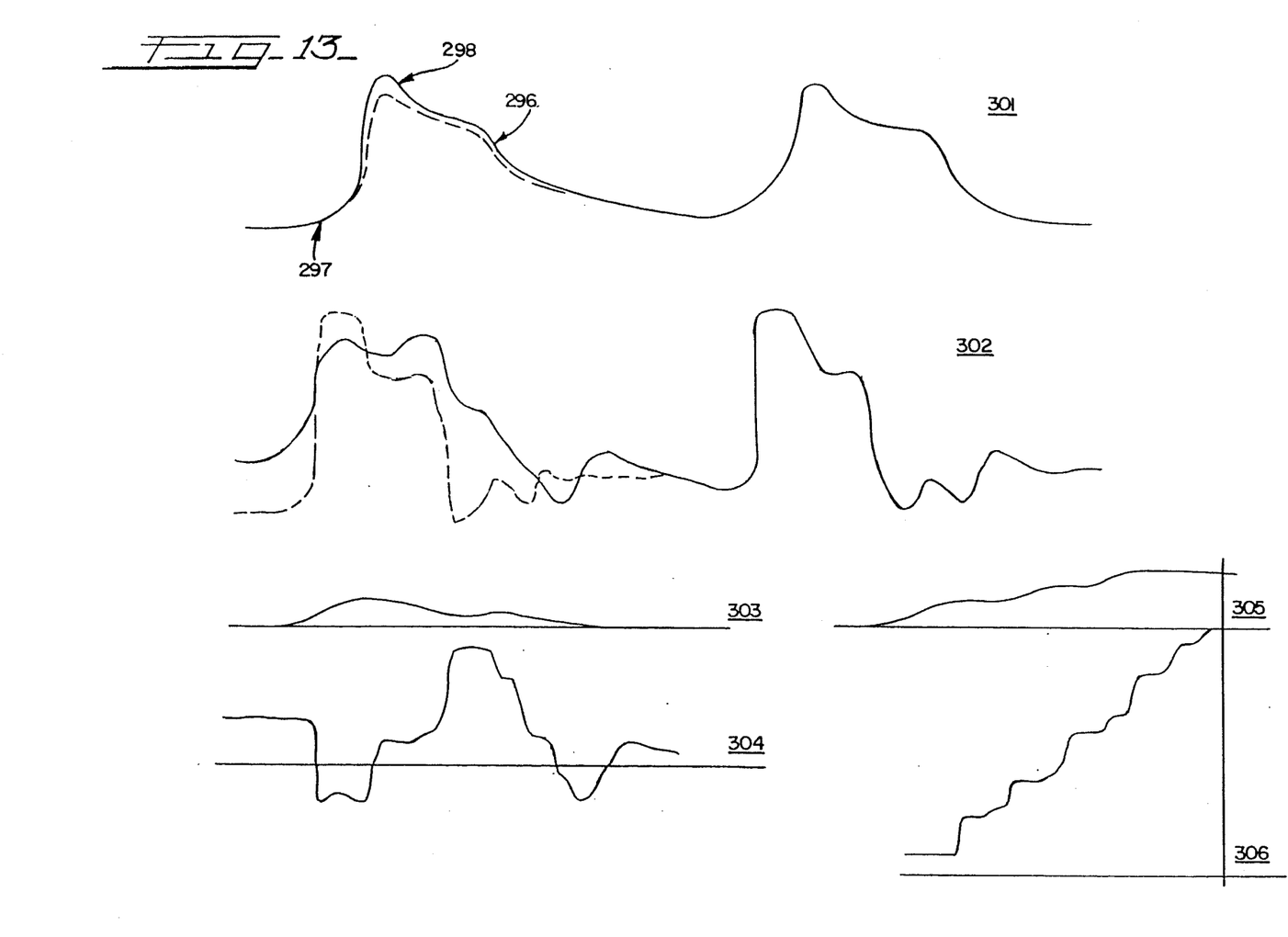

In order to give less weight to waveform pulses which are distorted by motion artifact, a criteria by which motion can be measured is established. FIG. 13 illustrates examples of waveforms which will be discussed in relation to these criteria.

Referring to FIG. 13, the algorithm routine 209 assumes that a plethysmograph 301 unaffected by motion varies only slightly between one pulse and the next. In addition, a change in the amplitude, not shape, of the pulse comprises the majority of the observed difference between one pulse and the next. A plethysmograph 302 containing artifact, however, differs greatly from the previous signal.

Signals 303 and 304 are obtained from plethysmographs 301 and 302, respectively, by subtracting the latest pulse from that immediately preceding it, in a point-by-point fashion. Note that the average amplitude of signal 303 is less than that of signal 304. Note further that the value of signal 303 is principally constant; while that of 304 changes rapidly, and often.

The integrations of the change in these two signals are shown by signals 305 and 306. Note that the final value of integrated signal 306 is much higher than that of integrated signal 305. Thus, a good indication of the amount of motion present in a pulse is given by the integration of the absolute value of the derivative of the point-by-point difference between the current pulse and the preceding pulse, taken over the length of the pulse.

Figure 12:
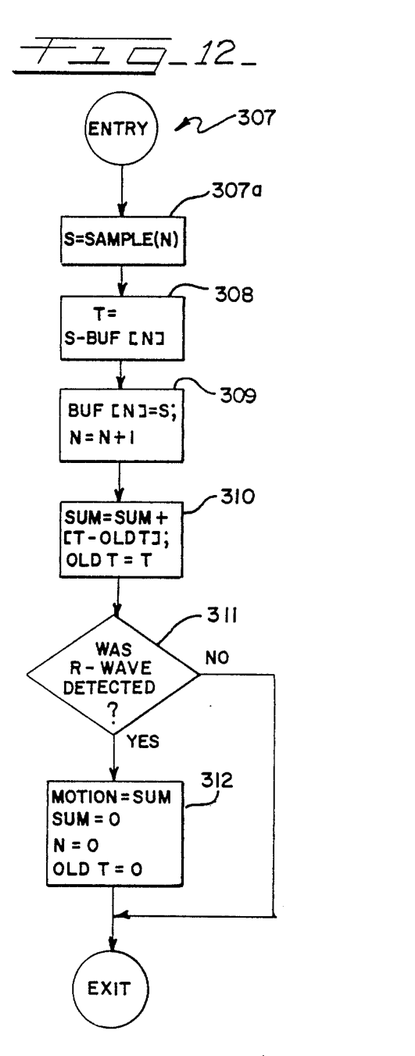
FIG. 12 is a block diagram of the R-wave acquisition and motion determination algorithm.

FIG. 12 illustrates a flowchart of the algorithm routine 307 which acquires a plethysmographic waveform while, simultaneously, determining whether or not the waveform is unduly affected by motion. This algorithm routine 307 sums the change in succeeding, point-by-point differences, taken between the pulse being currently acquired and the previous pulse.

Referring to the top of this flowchart, block 307a samples the plethysmograph. Block 308 computes the difference between the current point and, the corresponding point in the last pulse. Block 309 then inserts the current point into the buffer. Next, block 310 sums the absolute value of the difference between the last difference and the current difference. Decision diamond 311 then checks for the occurrence of an R-wave spike which would be detected by the R-wave detection algorithm routine 208. If a spike was detected, block 312 saves the accumulated sum as an indication of the level of motion present in the pulse, and initializes the variables to prepare for the next pulse.

The ensemble averaging algorithm routine 209 utilizes a variable-weight average in order to provide flexibility over a broad spectrum of pulsatile waveforms. It attempts to give large weight to waves which are largely motion-free, while diminishing the weight given to those which have motion. Additionally, if a low perfusion situation is detected, less weight is given to all pulses until several strong pulses are found. Furthermore, the algorithm routine 209 takes into account the pulse rate when determining the averaging weight. Since the averaging occurs each time a beat is detected, more averaging can be used on a patient with a fast pulse rate than one with a slow pulse rate while maintaining a constant response time. More averaging is needed in cases of motion artifact and low perfusion because the signal-to-noise ratio of these pulses is less than with normal pulses.

Figure 14:
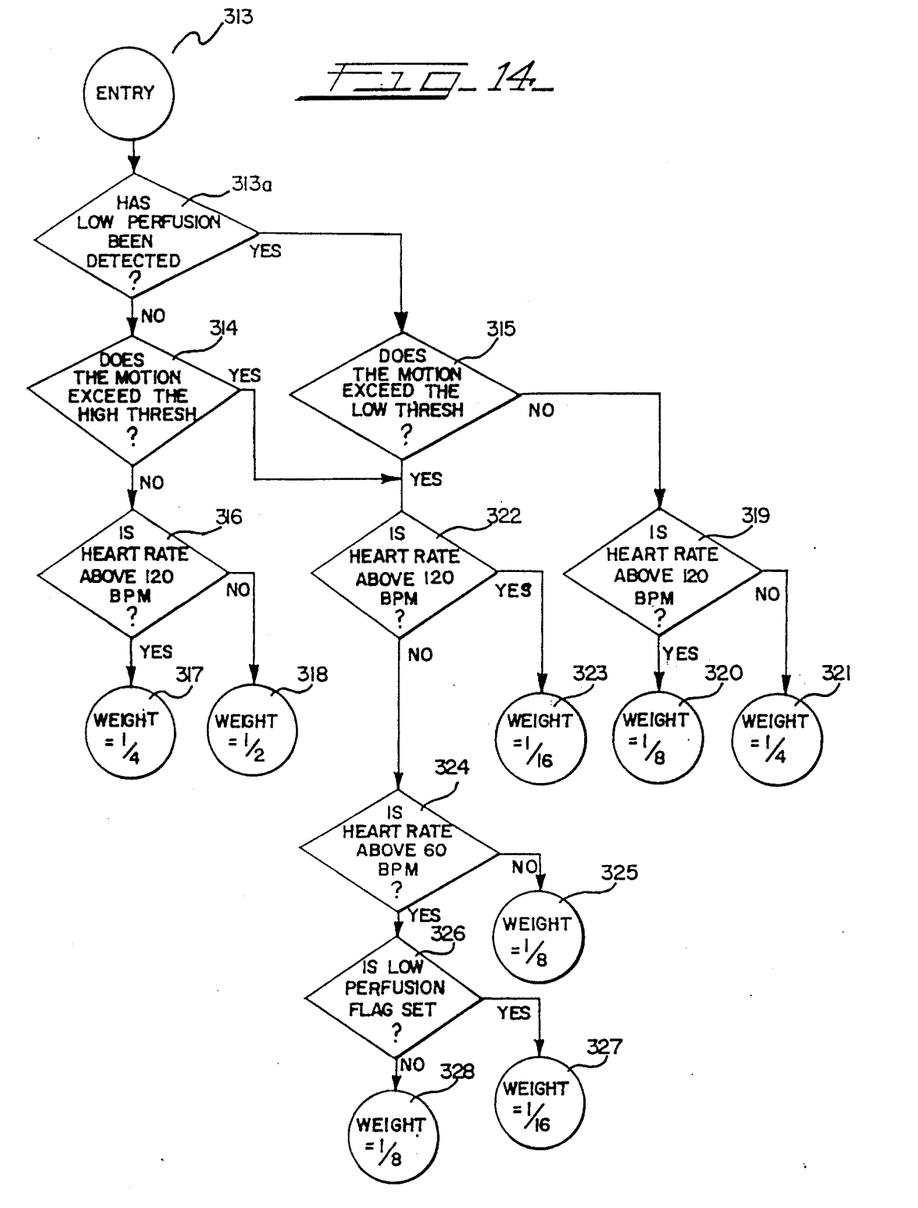
FIG. 14 is a block diagram illustration of the pulsatile waveform weight determination algorithm.

It is known generally that ensemble averaging with a set of N waveforms increases signal-to-noise level by a factor of the square root of N for uncorrelated, random noise. Thus, ensemble averaging will decrease the influence of uncorrelated motion artifact and will enhance a low perfusion signal which may be buried in noise at the expense of response time. A weight determination algorithm routine 313, for which a flowchart is shown in FIG. 14, intelligently trades response time for signal-to-noise ratio. At the same time, a maximum limit on response time is set in order to ensure that the displayed saturation value is reasonably current.

The weight determination algorithm routine 313 used to determine the appropriate ensemble average weighting for a newly acquired waveform is shown in FIG. 14. This algorithm routine 313 uses two empirically determined thresholds to determine whether the level of motion is significant. One of these thresholds applies during normal perfusion, while the other is used in cases of low perfusion.

In this algorithm routine 313, decision diamond 313a determines which of the two thresholds should be used by checking if low perfusion has been detected. If low perfusion has not been detected, decision diamond 314 checks the motion against threshold 1. If significant motion is not found, decision diamond 316 checks whether the heart rate is above 120 bpm. If it is, block 320 assigns an average weight of $\frac{1}{2}$. Otherwise, block 321 assigns an average weight of $\frac{1}{4}$.

If significant motion is found as a result of tests by either decision diamond 314 or 315, decision diamond 322 checks whether the heart rate is above 120 bpm. If it is, block 323 assigns a weight of 1/16. Otherwise, decision diamond 324 checks whether the heart rate is above 60 bpm. If it is not, block 325 assigns a weight of $\frac{1}{8}$. If it is, the software differentiates between low perfusion with motion and motion alone. Decision diamond 326 checks the low perfusion flag and, if it is set, block 327 assigns a weight of 1/16. Otherwise, block 328 assigns a weight of $\frac{1}{8}$.

Note that the heart rate used by this algorithm routine 313 is simply the time elapsed from the last accepted pulse to the current pulse. If a pulse was skipped as a result of amplifier saturation or other abnormalities, the heart rate used is lower and results in a larger weight being assigned. This has the effect of preserving response time in the case where poor signal quality causes some of the pulses to be rejected.

Figure 15:
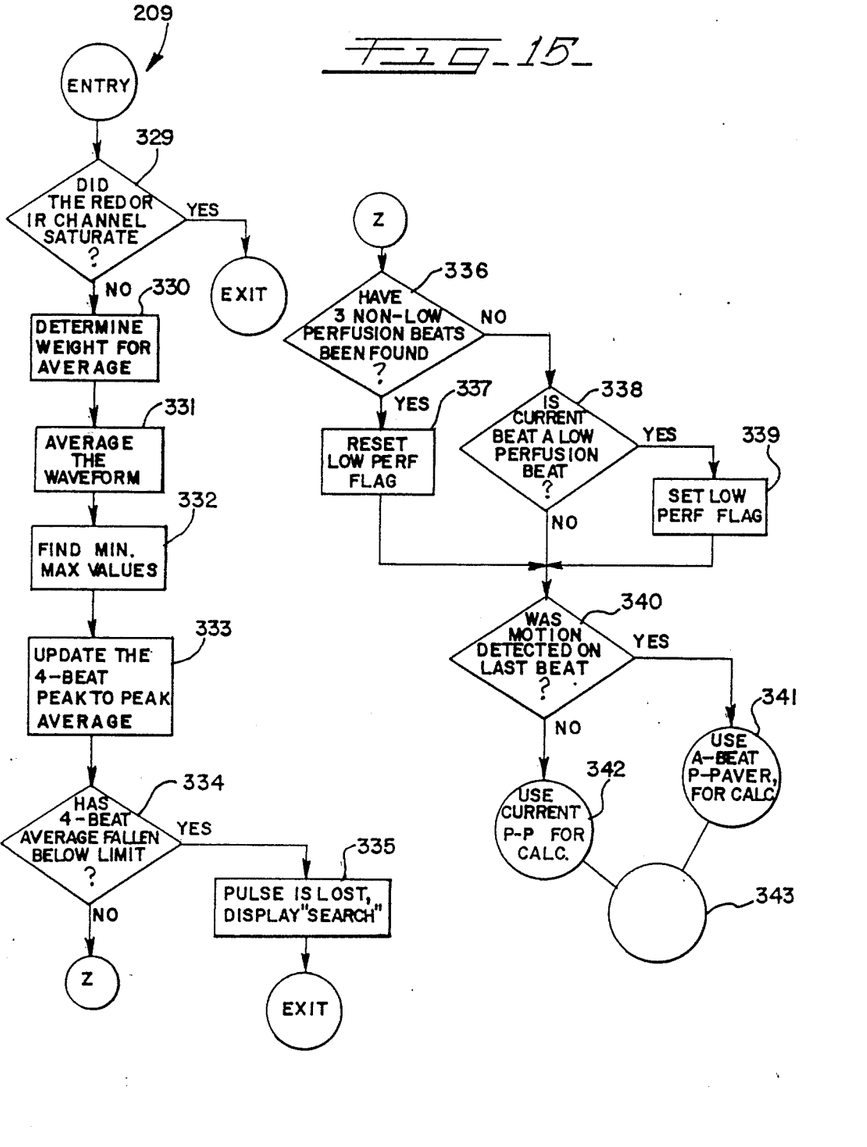
FIG. 15 is a block diagram of the ensemble averaging algorithm in the oximeter embodying features of the invention.

Finally, FIG. 15 is a flowchart of the ensemble averaging algorithm routine 209. First, decision diamond 329 determines if optical pulse processing circuitry 205 has saturated during the last pulse. If it has not, block 330 determines the appropriate weight for the waveform employing the weight determination algorithm routine 313 previously described. Block 330 averages the buffered waveform with the composite averaged waveform stored in the microcomputer memory, using a tail-weight average of the form $W \times NEW + (1-W) \times COMPOSITE$, with W being the averaging weight.

Next, block 332 finds the minimum and maximum values for the averaged waveform. Because the averaged pulses are of varying duration, some pulses will overlay more points of the averaged waveform than will others. Thus, the tail of the averaged waveform may not accurately reflect the most recent plethysmographic information. However, since the information desired is simply the peak-to-peak amplitude of the pulse, there is no need to rely on any information beyond the wave peak.

In order to ensure that any erroneous information contained within the tail of the waveform does not corrupt the peak-to-peak measurement, the waveform is searched only up to the minimum length of the last eight pulses. After determining the minimum and maximum values, block 333 updates the four-beat average of peak-to-peak values.

Decision diamond 334 then checks to ensure that the average has not fallen below the minimum low perfusion threshold. If it has, the pulse is considered lost and block 335 displays a message to this effect. Otherwise, decision diamond 336 checks if three non-low perfusion beats have been found. If so, block 337 resets the low perfusion flag. If not, decision diamond 338 checks if the current beat is a low perfusion beat. If it is, block 339 sets the low perfusion flag.

Decision diamond 340 then checks to determine whether motion was detected on the last beat. If it was, block 341 sends the four-beat, peak-to-peak average to calculation algorithm routine 210. Otherwise, block 342 sends the last peak-to-peak value to the routine 210. Block 343 then signals the routine 210 that a beat has been found.

The saturation calculation algorithm routine 210 then calculates oxygen saturation in a known manner. For an example of a calculation routine and process which may be used, reference is made to the copending application of Bahr et al., Ser. No. 06/771,217, filed Aug. 30, 1985, entitled Oximetry Method and Apparatus, and assigned to the same assignee as the present invention.

The oxygen saturation reading is displayed on a screen 204, as has been pointed out. The screen 204 is a liquid crystal display (LCD) screen with, as a result of its LCD makeup, the capability of displaying waveforms.

According to the invention, the oximeter 200 alternatively presents four different information displays. The LCD screen presents a digital display of oxygen saturation and pulse rate as a first alternative. It presents an ECG waveform display as a second alternative, and a plethysmograph waveform display as a third alternative, and a combination of the two as a fourth alternative, each together with oxygen saturation and pulse rate digital display. As a fifth alternative, an oxygen saturation trend graph may be displayed, together with instantaneous digital display of saturation.

While the preferred embodiment of the invention has been disclosed, it is understood that the invention is not limited to the disclosed example. Modifications in addition to those discussed can be made without departing from the invention. The scope of the invention is indicated in the appended claims, and all changes that come within the meaning and range of equivalency of the claims are therefore intended to be embraced therein.

We claim:

1. An improved method for determining the oxygen saturation level of a patient's blood, comprising the steps of:
    (a) optically measuring the patient's arterial blood flow so as to produce a series of optical pulses which are a measure of arterial pulses as well as patient motion and other artifact;
    (b) detecting the arterial heartbeat of the patient;
    (c) averaging a series of optical pulses within a time frame determined by the arterial heart-beat to derive an average optical pulse; and
    (d) determining the oxygen saturation level of the blood based upon the average optical pulse.

2. The improved method of claim 1 further characterized in that:
    (a) said averaging is performed by ensemble averaging a series of optical pulses.

3. The improved method of claim 2 further characterized by and including the steps of:
    (a) distinguishing pulses which are contaminated with motion artifact; and
    (b) applying a varying degree of averaging to pulses contaminated with motion artifact as compared with at least selected other pulses.

4. The improved method of claim 2 further characterized by and including the steps of:
    (a) distinguishing pulses which are the result of low perfusion arterial pulsation; and
    (b) applying a varying degree of averaging to pulses which are the result of low perfusion arterial pulsation as compared with at least selected other pulses.

5. The improved method of claim 2 wherein step (b) comprises the step of:
    (a) detecting the arterial heartbeat by obtaining an ECG, R-wave signal from the patient.

6. The improved method of claim 5 wherein step (c) comprises the step of:
    (a) utilizing the R-wave signal to determine the time frame for said ensemble averaging.

7. The improved method of claim 6 wherein step (b) comprises the step of:
    (a) locating and amplifying characteristics of the ECG signal waveform which are inherent in QRS complexes while inhibiting those that are not.

8. An improved method for determining the oxygen saturation level of a patient's blood, comprising the steps of:
    (a) optically measuring the patient's blood flow by passing two different wavelength beams of light through the patient's tissue whereby they are modulated by said blood flow and detecting the pulse waveforms of the light so modulated;
    (b) detecting the ECG, R-wave signal produced by the arterial heartbeat of the patient;
    (c) identifying and determining the position of the spikes associated with said R-wave;
    (d) averaging a series of said pulse waveforms for each wavelength within a time frame determined by the relationship of the R-wave spikes to derive an average optical pulse waveform; and
    (e) determining the oxygen saturation level of the blood based upon the average optical pulse waveform for both wavelengths.

9. The improved method of claim 8 further characterized in that:
    said averaging is performed by ensemble averaging said series of pulse waveforms.

10. The improved method of claim 9 further characterized by and including the steps of:

(a) distinguishing pulse waveforms which are contaminated with motion artifact or low perfusion arterial pulsation;
(b) applying a varying degree of averaging to different pulse waveforms depending upon the degree of presence or absence of artifact or evidence of low perfusion.

11. A pulse oximeter for measuring the oxygen saturation level in a patient's blood, comprising:
  (a) means for optically detecting blood flow in a patient, including arterial pulses and artifact, as waveforms;
  (b) means for detecting the arterial pulse of the patient;
  (c) means for averaging a plurality of said waveforms within a time frame determined by the detected arterial pulse to generate an average waveform; and
  (d) means for determining the oxygen saturation level of the blood based on the average waveform.

12. The oximeter of claim 11 further characterized in that:
  (a) said arterial pulse detecting means detects ECG waveforms.

13. The oximeter of claim 12 further characterized by and including:
  (a) microprocessor means which identifies R-wave spikes in said ECG waveforms and employs them in said averaging means.

14. The oximeter of claim 13 further characterized in that:
  (a) said averaging means effects ensemble averaging of a predetermined number of said optically detected waveforms.

15. The oximeter of claim 12 further characterized by and including:
  (a) means for displaying said optically detected waveforms; and
  (b) means for displaying said ECG waveforms.

* * * * *

UNITED STATES PATENT AND TRADEMARK OFFICE
CERTIFICATE OF CORRECTION

PATENT NO. : 4,960,126

DATED : October 2, 1990

INVENTOR(S) : Brendan Conlon et al

It is certified that error appears in the above-identified patent and that said Letters Patent is hereby corrected as shown below:

In Column 3, line 20, after "FIG." please insert --13--.

Signed and Sealed this

Thirtieth Day of March, 1993

Attest:

STEPHEN G. KUNIN

Attesting Officer    Acting Commissioner of Patents and Trademarks